US005612206A

United States Patent [19]
Valerio et al.

[11] Patent Number: 5,612,206
[45] Date of Patent: Mar. 18, 1997

[54] RETROVIRUS INFECTING PRIMATE BONE MARROW CELLS AND HARVESTING BOTH NON-ADHERENT AND ADHERENT CELLS

[75] Inventors: Domenico Valerio, Leiden; Victor W. van Beusechem, Amsterdam, both of Netherlands

[73] Assignee: Introgene B.V., Netherlands

[21] Appl. No.: 211,342

[22] PCT Filed: Oct. 5, 1992

[86] PCT No.: PCT/NL92/00177

§ 371 Date: Jun. 21, 1994

§ 102(e) Date: Jun. 21, 1994

[87] PCT Pub. No.: WO93/07281

PCT Pub. Date: Apr. 15, 1993

[30] Foreign Application Priority Data

Oct. 4, 1991 [NL] Netherlands .................... 9101680

[51] Int. Cl.$^6$ .................... C12N 15/00; C12N 5/00

[52] U.S. Cl. .................... 435/172.3; 435/373; 935/57

[58] Field of Search .................... 424/93.2; 435/246.2, 435/172.3, 240.1; 935/57

[56] References Cited

PUBLICATIONS van Beusechem et al (1990) J. Exp. Med. 172, 729–736.
Markowitz et al (1988) J. Virol. 62, 1120–1124.

*Primary Examiner*—Deborah Crouch
*Attorney, Agent, or Firm*—Dvorak and Traub

[57] ABSTRACT

A method is described for preparing primate bone marrow cells containing a DNA sequence of interest the method being first the isolation of bone marrow cells from a primate and then co-culturing the bone marrow cells with retrovirus producer cells. The retrovirus contains the DNA sequence of interest and infects the bone marrow cells during co-culture. To obtain bone marrow cells that contain the DNA sequence of interest, non-adherent bone marrow cells and adherent cells are harvested.

13 Claims, No Drawings

RETROVIRUS INFECTING PRIMATE BONE MARROW CELLS AND HARVESTING BOTH NON-ADHERENT AND ADHERENT CELLS

FIELD OF THE INVENTION

The invention concerns the field of gene therapy and more particularly relates to a method for genetically modifying bone marrow cells of primates, and to cells that produce recombinant retroviral vectors that can be used in such a method.

PRIOR ART

Introduction

Developments in the field of molecular biology have led to a better understanding of the genetic basis underlying the development of a large numbers of disorders. It is expected that the genes which are associated with the diseases that occur most frequently will have been identified, cloned and characterized before the end of this century.

So far, molecular genetics has contributed to medicine by the development of diagnostic tools and methods and the biotechnological production of pharmaceuticals. It may be expected, however, that it will also be possible to use the increasing knowledge of genetics for an essentially new therapeutic treatment, the so-called gene therapy. The purpose of gene therapy is to treat disorders by genetically modifying somatic cells of patients. The uses of gene therapy are not limited to hereditary disorders; the treatment of acquired diseases is also considered to be one of the possibilities. Although this field of study is still in a preliminary stage and must be developed, therapeutic possibilities are in the distance which can drastically improve medicine in the future (1–3).

An important cell type for gene therapy purposes is the so-called haemopoietic stem cell which is situated in the bone marrow and is the precursor cell of all circulating blood cells. This stem cell can also multiply itself without losing its differentiating ability. The underlying idea of a gene therapy directed to these cells is that gene transfer to (a limited number of) stem cells may already be sufficient to replace the entire blood-forming tissue with genetically modified cells for a lifetime (4). This would enable treatment not only of diseases that are caused by a (hereditary) defect of blood cells, but also of diseases that are based on the inability to make a certain protein: the modified blood (forming) system could be a constant source of the protein, which could do its work at the places where necessary. It is also possible, with the introduction of genetic material into the blood system, to obtain resistance against infectious agents or even to overcome a predisposition to chronic diseases, such as rheumatism or diabetes.

Finally, it can be noted that in the treatment of some diseases it is to be preferred or necessary that the gene transfer to stem cells is performed on bone marrow cell populations from which certain cell types have been removed. One could for instance consider the use of gene therapy in the treatment of leukemia, in which case there should not occur any gene transfer to the leukemic cells.

Retroviral Vectors

One of the conditions for the realization of such a bone marrow gene therapy protocol is a technique by which genes can be incorporated into the chromosomes of target cells, in such a manner that those genes are also passed on to the daughter cells and that the desired protein product is produced in those cells.

In the invention described here, for this purpose use is made of recombinant retroviruses that carry with them the genes to be introduced and are capable of delivering them in mammalian cells. They make use of the natural characteristic of retroviruses to integrate efficiently and stably into the genome of the infected cell, but cannot themselves cause any productive infection anymore because they are replication-defective and are not contaminated with wild-type viruses (5, 6).

The recombinant retroviruses which are used within the framework of the present invention are all based on murine leukemia viruses (MuLV; 7). For gene therapy in humans, use will be made of so-called amphotropic retroviruses which have a broad host-specificity and can infect primate cells, in addition to murine cells.

For the production of recombinant retroviruses, two elements are required:

a) the so-called retroviral vector, which, in addition to the gene (or genes) to be introduced, contains all DNA elements of a retrovirus that are necessary for packaging the viral genome and the integration into the host genome, and b) the so-called packaging cell line which produces the viral proteins that are necessary for building up an infectious recombinant retrovirus (8).

As the presence of replication-competent viruses in a gene therapy protocol is considered highly undesirable, most modern packaging cell lines are so constructed that the risk of recombination events whereby a replication-competent virus is generated, is minimized. This is effected by physically separating into two parts the parts of the virus genome that code for viral proteins and introducing them into the cell line separately (9–11).

As the presence of both constructs is essential to the functioning of the packaging cell line and chromosomal instability occurs regularly, it is of great importance for the routine use of such cells in gene therapy procedures that by means of a selection medium selection for the presence of the constructs can be provided for. Therefore these constructs are often introduced by means of a so-called cotransfection whereby both viral constructs are transfected together with a dominant selection marker. The possibility of selection thus provided is certainly not a trivial requirement, considering for instance the observation that we and various other research groups made, that virus-producing cells based on the packaging cell line ψCRIP (9) are not stable. That is to say that they are no longer resistant to the relevant selection media and during cultivation lose their capacity to produce retroviruses. One example, of importance for the present invention, is the so-called POC-1 cell line which was produced by us on the basis of ψCRIP cells (12) and on account of its instability cannot be used for gene therapy on a routine basis. Therefore, in the invention described here, use is made of packaging cells which, by means of a dominant selection culture, will continue to produce stable virus.

Genetic Modification of the Haemopoietic System

Studies in mice have demonstrated that using amphotropic retroviral vectors, bone marrow stem cells can be provided with a new gene. After transplantation of these modified cells into lethally irradiated mice, the new gene could also be demonstrated for long periods in many different blood cell types of the transplanted animals (12).

Previous problems with regard to the non-expression of the newly introduced genes were solved by us by using a retroviral vector in which the expression of the gene of choice, is driven by a retroviral promoter whose expression-specificity has been changed by means of a replacement of the so-called enhancer (12, 13). In the present invention, these vectors are called LgXL(ΔMo+PyF101), wherein X represents the code of a gene yet to be filled in.

Preclinical Studies in Nonhuman Primates

Before the results obtained from research into gene transfer into the blood-forming organ of mice can be translated into an eventual use of gene therapy in the clinic, a number of essential questions must be answered by studying a relevant preclinical model. First of all, it will have to be demonstrated that efficient gene transfer is also possible to blood-forming stem cells of higher mammals, in particular primates. Moreover, genetic modification coupled with autologous bone marrow transplantation in primates requires complex logistics which cannot be studied in mice. The organization of the blood-forming organs of mice and humans can only be compared to a certain extent and it will be clear that the sizes of the two species, and hence the numbers of cells involved in transplantation, differ considerably.

The experimental animal model that is eminently suitable for preclinical gene therapy studies is the nonhuman primate, in particular the rhesus monkey, partly because the current bone marrow transplantation protocols in the clinic are principally based on data obtained from experiments with bone marrow from the rhesus monkey. Gene therapy procedures using bone marrow cells can be tested in this animal model by taking bone marrow, modifying this genetically by means of recombinant retroviruses and subsequently transplanting it back autologously (i.e. into the same monkey) after the endogenous bone marrow cells have been eradicated by means of irradiation.

To date, such experiments have met with little success with regard to:

a) the haemopoietic regeneration that could be effected with the infected bone marrow, and b) the in vivo stability of the genetic modification.

re a): For an efficient gene transfer by means of retroviral vectors, a direct exposure of the bone marrow cells to be infected to the virus-producing cells is required. This occurs by means of a so-called cocultivation wherein the virus-producing cells are adhered to the bottom of a culture bottle and the bone marrow cells are seeded on top thereof. Following cocultivation, the non-adherent bone marrow cells are subsequently harvested and used as transplants.

In the data published to date, this so-called cocultivation of the two cell types has always been associated with a drastic loss of in vivo regenerating capacity of the bone marrow cells (14–16), so that a clinical application is precluded.

The present invention shows in an example that under controlled conditions, with the virus-producing cells described here a cocultivation can occur without such a regeneration loss.

re b): None of the studies published to date are sufficiently interpretable as regards genetic modification, since they invariably involved the use of virus preparations in which replication-competent virus was present. Via a so-called "rescue", this may lead to a spread of the recombinant virus genome after the cells have been transplanted, so that it remains unclear whether the modified cells are offspring of infected bone marrow cells.

In the first reported study (14, 15), in 19 monkeys an autologous transplantation was performed with bone marrow cells infected with different retroviral vectors containing the gene for neomycin resistance (neo$^r$) or dihydrofolate reductase (DHFR), or with a virus in which neo$^r$ and the gene for adenosine deaminase (ADA) are located together, produced by cells that also produce replication-competent virus.

Two gene transfer procedures were utilized, the cocultivation procedure described under re a) or an infection with virus supernatant that can be harvested from the virus-producing cells. The cocultivation was associated with the inability to arrive at a haemopoietic regeneration after autologous transplantation. As a result, only three out of the 13 monkeys survived this procedure. None of the surviving monkeys showed any signs of genetic modification in vivo. Complete haemopoietic reconstitution could be obtained in the six monkeys that received supernatant-infected bone marrow and in four of these animals the gene could be demonstrated. However, genetic modification remained low and transient. Nor could it be precluded that the observed modification had occurred in long-living T-cells which did not generate from the bone marrow cultured in vitro, but were already present as contaminations in the infected bone marrow.

In the second study (16) bone marrow from rhesus monkeys was cocultivated with cell lines that produce neo$^r$-containing viruses. In this study, two, only the provirus could be demonstrated in vivo after infection by means of a virus-producing cell line that produce contaminatory helper viruses. In this setting, no long-term studies could be performed because again the bone marrow proved incapable of reconstituting the haemopoietic system.

Our invention shows in an example that bone marrow cells cocultivated with the virus-producing cells described here are capable of genetically modifying the haemopoietic system of primates after autologous transplantation. This modification was observed for a prolonged period in several blood cell types including granulocytes, which have a very short lifetime (approximately 8 hours). With the method described by us, these results can also be obtained when the bone marrow has previously been enriched for haemopoietic stem cells by removal of most other (riper) bone marrow cells. These data demonstrate our capacity to infect very primitive cells and show that it is possible to carry out gene therapy using such modified bone marrow cells.

Brief Description of the Essence of the Invention

The invention provides a method for genetically modifying bone marrow cells of primates, comprising isolating bone marrow cells from a primate and, by means of a cocultivation, exposing the isolated bone marrow cells to cells that produce a recombinant amphotropic retrovirus with a genome based on a retroviral vector which contains the genetic information to be introduced into the bone marrow cells. It is here preferred that the genome of the recombinant amphotropic retrovirus is based on a retroviral vector which is derived from a viral MuLV vector.

The term "primates" is understood to mean all primates, including man. Preferably, the gene therapy concerns man.

According to the invention, it is preferred that the retroviral vector comprises two LTRs (long terminal repeats)

derived from a viral MuLV vector and the 5' part of the gag gene of a MuLV. The MuLV sequences are preferably derived from the viral Mo-MuLV vector (Moloney Murine Leukemia Virus), while at least the 3'-LTR is a hybrid LTR which contains the PyF101 enhancer instead of the Mo-MuLV enhancer. To this end, preferably the retroviral vector pLgXL(ΔMo+PyF101) is used, wherein X represents the genetic information to be introduced into the bone marrow cells.

According to the invention, the cells that produce the recombinant amphotropic retrovirus are preferably recombinant mammalian cells which contain and express the gag, pol and env genes of MuLV. The env gene is preferably derived from an amphotropic MuLV. The gag, pol and env genes of MuLV in the recombinant mammalian cells are preferably distributed over at least two different eukaryotic expression vectors. Further, it is preferred that each packaging construct is associated with a selectable marker gene. Preferably, as recombinant mammalian cells GP+envAM12 cells are used, while it is further preferred that the cells that produce a recombinant amphotropic retrovirus contain several copies of the retroviral vector.

According to the invention, it is further preferred that the cocultivation of bone marrow cells with cells that produce amphotropic retrovirus occurs in the presence of serum and at least one haemopoietic growth factor. After the cocultivation, the non-adherent bone marrow cells are preferably harvested together with adherent bone marrow cells. In some cases it is preferred that bone marrow cell populations are used which have been priorly enriched for haemopoietic stem cells.

The invention further provides cells that produce a recombinant amphotropic retrovirus with a genome based on a retroviral vector, preferably one which is derived from a viral MuLV vector, which contains genetic information that is suitable to be introduced into bone marrow cells of a primate according to the method described herein.

DETAILED DESCRIPTION OF THE INVENTION

The invention removes the above-mentioned drawbacks with regard to the required stability of the virus-producing cells by providing cells that can be selected for the presence of the viral constructs and produce a recombinant amphotropic retrovirus whose genome is composed of the recombinant retroviral vector pLgXL(ΔMo+PyF101) wherein X represents an inserted gene coding for a protein which is of importance for gene therapy.

The invention further provides a method for introducing a gene X into bone marrow cells, whereby bone marrow cells of a primate are brought together in a cocultivation with the aforementioned selectable virus-producing cells that produce a recombinant amphotropic retrovirus whose genome is composed of the recombinant retroviral vector pLgXL(ΔMo+PyF101) with gene X inserted therein.

The invention is comprised of a number of essential components:

a) the recombinant retroviral vector pLgXL(ΔMo+PyF101), b) the virus-producing cell line, and c) the method by which bone marrow cells or purified stem cells of a primate can be provided with gene X.

Re a) Recombinant Retroviral Vector pLgXL(ΔMo+PyF101)

The recombinant retroviral vector is comprised of a number of essential components, viz.:

i) plasmid sequences necessary for propagation of the vector in *E. coli* bacteria such as for instance pBR322 (17) or a vector from the pUC series (18); on these, both an origin of replication and a selectable gene (for instance for ampicillin of tetracyclin resistance) must be present.

ii) DNA elements originating from a MuLV which are necessary in cis for the packaging, reverse transcription and integration of the retroviral genome; these include two so-called Long Terminal Repeats (LTR) and the so-called packaging sequences. In the LTR a modification has been provided by replacing the enhancer originating from MuLV with the enhancer of the polyoma virus strain PyF101 (19). In the plasmid construct, it is not necessary that this modification is present in both LTRs; only the 3' LTR must be provided therewith since that portion of the LTR ends up in both LTRs after a viral infection (12, 13).

iii) the 5' part of the MuLV gag-encoding sequences such as present in the vector N2 (20), so as to effect a higher viral titre. Optionally, herein the ATG initiation codon of gag can be mutated by means of site-directed mutagenesis, in such a manner that no translation start can occur thereon anymore.

iv) the encoding sequences of gene X. These are genes that code for proteins which can be of importance for gene therapy, i.e., all genes associated with hereditary disorders wherein a therapeutic effect can be achieved by introducing an intact version of the gene into somatic cells. Most of them are documented in:

— McKusick, V. A. Mendelian inheritance in man, catalogs of autosomal dominant, autosomal recessive, and X-linked phenotypes. Eighth edition. John Hopkins University Press (1988).

— Stanbury, J. B., Wyngaarden, J. B., Frederickson, D. S., Goldstein, J. L. and Brown, M. S. The metabolic basis of inherited disease. Fifth edition. McGraw-Hill (1983).

Examples include:
genes associated with diseases of the carbohydrate metabolism such as for:

— fructose-1-phosphate aldolase
— fructose-1,6-diphosphatase
— glucose-6-phosphatase
— lysosomal α-1,4-glucosidase
— amylo-1,6-glucosidase
— amylo-(1,4:1,6)-transglucosidase
— muscular phosphorylase
— liver phosphorylase
— muscular phosphofructokinase
— phosphorylase-b-kinase
— galactose-1-phosphate uridyl transferase
— galactokinase
— all enzymes of the pyruvate dehydrogenase complex
— pyruvate carboxylase
— 2-oxoglutarate glyoxylate carboligase
— D-glycerate dehydrogenase genes associated with diseases of the amino acid metabolism such as for:

— phenylalanine hydroxylase
— dihydrobiopterin synthetase
— tyrosine aminotransferase
— tyrosinase
— histidase
— fumarylacetoacetase

- glutathione synthetase
- γ-glutamylcysteine synthetase
- ornithine-δ-aminotransferase
- carbamoylphosphate synthetase
- ornithine carbamyltransferase
- argininosuccinate synthetase
- argininosuccinate lyase
- arginase
- L-lysine dehydrogenase
- L-lysine ketoglutarate reductase
- valine transaminase
- leucine isoleucine transaminase
- "branched chain" 2-keto acid decarboxylase
- isovaleryl CoA dehydrogenase
- acyl-CoA dehydrogenase
- 3-hydroxy-3-methylglutaryl CoA lyase
- acetoacetyl CoA 3-ketothiolase
- propionyl CoA carboxylase
- methylmalonyl CoA mutase
- ATP:cobalamine adenosyltransferase
- dihydrofolate reductase
- methylene tetrahydrofolate reductase
- cystathionine β-synthase
- sarcosine dehydrogenase complex
- proteins belonging to the glycine cleavage system
- β-alanine transaminase
- serum carnosinase
- cerebral homocarnosinase genes associated with diseases of fat and fatty acid metabolisms such as for:
- lipoprotein lipase
- apolipoprotein C-II
- apolipoprotein E
- other apolipoproteins
- lecithin cholesterol acyltransferase
- LDL receptor
- liver sterol hydroxylase
- "Phytanic acid" α-hydroxylase genes associated with lysosomal defects such as for:
- lysosomal α-L-iduronidase
- lysosomal iduronate sulphatase
- lysosomal heparan N-sulphatase
- lysosomal N-acetyl-α-D-glucosaminidase
- lysosomal acetyl CoA:α-glucosaminide N-acetyltransferase
- lysosomal N-acetyl-α-D-glucosaminide 6-sulphatase
- lysosomal galactosamine 6-sulphate sulphatase
- lysosomal β-galactosidase
- lysosomal arylsulphatase B
- lysosomal β-glucuronidase
- N-acetylglucosaminylphosphotransferase
- lysosomal α-D-mannosidase
- lysosomal α-neuraminidase
- lysosomal aspartylglycosaminidase
- lysosomal α-L-fucosidase
- lysosomal acid lipase
- lysosomal acid ceramidase
- lysosomal sphingomyelinase
- lysosomal glucocerebrosidase
- lysosomal galactosylceramidase
- lysosomal arylsulphatase A
- α-galactosidase A
- lysosomal acid β-galactosidase
- α-chain of the lysosomal hexosaminidase A genes associated with diseases of the steroid metabolism such as for:
- 21-hydroxylase
- 11β-hydroxylase
- androgen receptor
- steroid 5α-reductase
- steroid sulphatase genes associated with diseases of the purine and pyrimidine metabolism such as for:
- phosphoribosylpyrophosphate synthetase
- hypoxanthine guanine phosphoribosyltransferase
- adenine phosphoribosyltransferase
- adenosine deaminase
- purine nucleoside phosphorylase
- AMP deaminase
- xanthine oxidase
- orotate phosphoribosyltransferase
- orotidine 5'-phosphate decarboxylase
- DNA repair enzymes genes associated with diseases of the porphirine and haemal metabolism such as for:
- uroporphyrinogene III cosynthase
- ferrochelatase
- porphobilinogene deaminase
- coproporphyrinogene oxidase
- proporphyrinogene oxidase
- uroporphyrinogene III synthase
- uroporphyrinogene decarboxylase
- bilirubine UDP-glucuronyltransferase
- catalase genes associated with diseases of the connective tissue, muscles and bone such as for:
- lysyl hydroxylase
- procollagen peptidase
- α1-antitrypsine
- dystrophine
- alkaline phosphatase
- guanosine nucleotide regulatory protein of the adenyl cyclase complex genes associated with diseases of the blood and blood-forming organs such as for:
- blood coagulation factor V
- blood coagulation factor VII
- blood coagulation factor VIII
- blood coagulation factor IX
- blood coagulation factor X
- blood coagulation factor XII
- blood coagulation factor XIII
- all other blood coagulation factors
- all genes associated with osteopetrosis such as for: "carbonic anhydrase II"

— thrombocytes membrane glycoprotein Ib
— thrombocytes membrane glycoprotein IIb-IIIa
— spectrin
— pyruvate kinase
— glucose-6-phosphate dehydrogenase
— NADH cytochrome $b_5$ reductase
— β-globin
— α-globin genes associated with diseases of transport systems such as for:
— lactase
— sucrase-α-dextrinase
— 25-hydroxyvitamin $D_3$-1-hydroxylase
— cystic fibrosis transport regulator genes associated with congenital immunodeficiencies such as for:
— the proteins of the complement system including B, C1q, C1r, C2, C3, C4, C5, C7, C8 and C10
— the inhibitor of C1, a component of the complement system
— the inactivator of C3b, a component of the complement system the genes for X-bound immunodeficiencies such as for:
— one of the enzymes of the NADPH oxidase complex
— myeloperoxidase
— the syndrome of Wiscott Aldrich and Ataxia Telangiectasia genes coding for hormones as well as the genes coding for their receptors such as for instance for:
— growth hormone Gene X also includes genes which (to date) have not been associated with a hereditary defect but with which gene therapy can be practised in some manner.

These include:
the gene for tyrosine hydroxylase
drug resistance genes such as for instance:
— the P-glycoprotein P170 (the so-called multi drug resistance gene mdr1)
— mdr 3
— dihydrofolate reductase (DHFR) and methotrexate resistant isotypes thereof
— metallothioneine
— aldehyde dehydrogenase (ALDH)
— glutathione transferase genes coding for all cytokins including for instance all interleukins and all interferons
genes coding for all growth factors
genes coding for all growth factor receptors
genes coding for all transplantation antigens such as for instance the major and minor histocompatibility antigens
genes capable of affording resistance against infectious organisms, such as for instance TAR decoys (21)
genes of infectious organisms which can be used for vaccination purposes such as for instance the envelope gene of HIV
genes which can be used for negative selection such as for instance the thymidine kinase gene of the Herpes simplex virus against which selection can be effected with substrates such as for instance gancyclovir or acyclovir (22, 42).

Re b) The Virus-producing Cells

In order to obtain a stable, selectable virus-producing cell line which produces the amphotropic recombinant retrovirus, pLgXL(ΔMo+PyF101) will have to be introduced into an amphotropic packaging cell line that can be selected for the presence of the DNA sequences which are of importance for the production of the viral proteins. One example of such a cell line is GP+envAm12 (11). It has been demonstrated, on the other hand, that ψCRIP is not selectable and unstable with respect to the virus production (9).

The selectable packaging cell line is based on mammalian cells and produces all viral proteins that are coded by the gag, pol and env genes of MulV. The env gene must originate from an amphotropic MuLV. In order to obtain expression of the aforementioned viral genes, they, while cloned in a eukaryotic expression vector, must be under control of a promoter active in the host, preferably a RNA polymerase II promoter, and be followed by a polyadenylation signal. On these so-called packaging constructs, all three viral genes may be present simultaneously as for instance described by Miller (23), but the genes may also occur separately on two expression vectors as described by Markowitz (11). This last is to be preferred because it reduces the chances of recombination events leading to helper virus formation.

As stated, an essential characteristic of the packaging cell line to be used for this invention is the possibility it provides of selecting for the presence of the above-mentioned packaging constructs. This can be achieved by effecting a physical association of the packaging constructs with a selectable marker gene. This association can be achieved by combining them in one vector (as done with pGag-PolGPT in reference (10)) or by means of a so-called cotransfection (review in for instance (24)). The successfully transfected cells can then be isolated by selecting for the marker gene. Since the cotransfected DNA fragments mostly end up ligated to each other at one place in the genome of the transfected cell (24)), the thus selected cells will mostly contain the packaging construct as well. In view of the fact that ψCRIP cells have been made in this way and, nevertheless, are not selectable, the last procedure is not always successful and the construction of vectors with the marker gene cloned into it is to be preferred.

As marker gene, genes coding for a large number of different proteins can be used. Widely used and preferred marker genes are: the neomycin resistance gene (25), the hygromycin resistance gene (26), the E. coli xanthine-guanine phosphoribosyl transferase (gpt) gene (27), the histidinol gene (28), the herpes simplex virus thymidine kinase gene (29) and the methotrexate resistant isotype of dihydrofolate reductase (30). These genes must also be under control of a suitable promoter, in particular a RNA polymerase II promoter, and be followed by a polyadenylation signal.

The introduction of pLgXL(ΔMo+PyF101) can be effected by means of various physical techniques such as calcium-phosphate precipitation, electroporation or lipofection (31–35). If the packaging cells cannot be selected for the presence of pLgXL(ΔMo+PyF101), use will be made of a selectable marker such as for instance an expression vector of the neomycin resistance gene which is transfected together with pLgXL(ΔMo+PyF101). The successfully transfected cells can then be selected by selecting for the marker gene. Since the DNA fragments mostly end up ligated to each other in one place in the genome of the transfected cell, the thus selected cells will mostly contain the retroviral vector as well.

A preferred procedure is the introduction of pLgXL(ΔMo+PyF101) via an infection. Since amphotropic viruses are not capable of infecting amphotropic packaging cells, use must be made of an ecotropic version of the recombinant retrovirus which is obtained by introducing the DNA initially via a physical technique into ecotropic packaging cells. Ecotropic virus produced by such cells can be used to infect amphotropic packaging cells whereafter the infected cells can be cloned and subsequently tested for their ability to produce virus.

Further, it is possible to obtain cell lines producing a higher titre of the virus by introducing several copies of the retroviral vector into the packaging cells using the so-called "ping-pong" method (36, 37). In this method, an ecotropic virus-producing cell line is cocultivated with amphotropic packaging cells, which can give rise to repeated infections. In order to enable the amphotropic cells to be cloned back after this cocultivation, they must be selectable with selective media in which the ecotropic packaging cells do not survive. By plating the cells in such medium, the proper virus-producing clones can be isolated and subsequently analysed for their capacity to produce the recombinant virus.

Re c) Method by which Bone Marrow Cells of a Primate can be Provided with Gene X, in such a Manner that the Regeneration Capacity of the Bone Marrow is Maintained and Autologous Transplantation of the Bone Marrow Cells Gives Rise to a Genetically Modified Haemopoietic System The above-mentioned recombinant retroviral vectors can be used for the efficient introduction of gene X into bone marrow cells of primates by exposing the last-mentioned cells to the virus-producing cells via a cocultivation. In the preferred method, this takes place for three to four days in the presence serum and one or more haemopoietic growth factors such as for instance interleukin 3 (IL-3). The method can further be used after the bone marrow has been enriched for haemopoietic stem cells, which is to be preferred in some cases. Following cocultivation, both the non-adherent and the adherent cells are harvested from the culture (the last-mentioned cells can be obtained by means of trypsinisation) and used as bone marrow transplant.

PRACTICAL EXAMPLE a) Production of Selectable Stable Recombinant Retrovirus-producing Cells In the practical example, use was made of the retroviral vector construct pLgAL(ΔMo+PyF101) (12), wherein A represents the human cDNA gene coding for adenosine deaminase (ADA). Twenty micrograms of this construct were transfected to the ecotropic packaging cell line GP+E-86 (10), according to the method described by Chen and Okayama (38). Prior to the transfection, the GP+E-86 cells had been cultured in medium containing 15 µg/ml hypoxanthine, 250 µg/ml xanthine and 25 µg/ml mycophenolic acid, so as to select for the preservation of the DNA sequences responsible for the production of the viral proteins. Transfectants that produced a functional human ADA enzyme were isolated by means of a selective culture in medium with a combination of 4 µM xylofuranosyl-adenine (Xyl-A) and 10 nM deoxycoformycin (dCF) (12).

Then, with the thus obtained cells a ping-pong culture as described by Kozak and Kabat (37) was initiated. To that end, $5\times10^3$ transfectants were mixed with an equal amount of GP+envAm12 amphotropic packaging cells (11) and cultured together in α-modified DMEM (Dulbecco's Modified Eagle's Medium) with 10% FCS (Fetal Calf Serum) and 8 µg/ml polybrene. The amphotropic packaging cells were also selected prior to use, for the preservation of the DNA sequences coding for the viral proteins (in the medium as described for GP+E-86 cells, with 200 µg/ml hygromycin B added thereto). The culture was expanded for two weeks, whereafter the amphotropic virus-producing cells were recovered using the resistance of these cells against hygromycin B. Individual GP+envAm12 clones that express functional human ADA and produce the viral proteins, were obtained by culturing limited cell numbers in medium containing all above-mentioned components in the amounts mentioned. In all, 12 of such clones were isolated and tested.

DNA analysis demonstrated that the clones contained several copies of the retroviral vector. The titre of the virus supernatants produced by the 12 clones was measured by exposing murine fibroblasts to dilutions of these supernatants and subsequently determining the number of fibroblasts that had acquired resistance against Xyl-A/dCF as a result hereof. The different clones produced between $3\times10^3$ and $2\times10^5$ infective virus particles per milliliter supernatant. The best clones produced 100 × more virus than the best amphotropic LgAL(ΔMo+PyF101) virus-producing cell line to date, which had been obtained via a single infection with ecotropic virus.

In order to obtain some idea about the most promising clone with regard to the use in bone marrow gene therapy procedures, rhesus monkey bone marrow was cocultivated for three days with each of the 12 virus-producing cell lines. Subsequently, the preservation of the capacity of the bone marrow to form haemopoietic colonies in vitro and the infection efficiency regarding the haemopoietic precursor cells, which are at the origin of these colonies, were determined. With some of the clones, infection efficiencies of up to 40–45% Xyl-A/dCF resistant precursor cells could be achieved, while none of the clones showed a clear toxicity towards these bone marrow cells.

On the basis of all aforementioned criteria, a cell line was chosen, which was called POAM-P1. This cell line was used to demonstrate in the practical example described under b the usefulness of the thus obtained virus procedures for the genetic modification of the blood-forming organ of primates.

b) Preclinical Test of a Bone Marrow Gene Therapy Procedure in Rhesus Monkeys with the Cell Line POAM-P1 Described Under a)

Rhesus monkey bone marrow was taken by puncturing the upper legs and suspended in HBSS/Hepes with 100 units heparin and 100 µg/ml DNase I. Cells having a density lower than 1.064 g/ml were obtained by successively performing a Ficoll separation and a BSA-density gradient centrifugation (39). These operations resulted in an enrichment of the cell population for haemopoietic stem cells by a factor of 10–20. The thus obtained bone marrow cells were introduced, in a concentration of $10^6$ cells per ml, into high glucose (4.5 g/liter) α-modified DMEM, containing 5% heat-inactivated monkey serum, 15 mg/ml BSA (Bovine Serum Albumin), $1.25\times10^{-5}$M $Na_2SeO_3$, 0.6 mg/ml iron-saturated human transferrin, 1 µg/ml of each of the following nucleosides: adenosine, 2'-deoxyadenosine, guanosine, 2'-deoxyguanosine, cytidine, 2'-deoxycytidine, thymidine and uridine, $1.5\times10^{-5}$M linoleic acid, $1.5\times10^{-5}$M cholesterol, $1\times10^{-4}$M β-mercaptoethanol, 0.4 µg/ml polybrene, 100 μg/ml streptomycin, 100 U/ml penicillin and 50 ng/ml of the recombinant rhesus monkey haemopoietic growth factor IL-3 (40). The thus obtained cell suspension was seeded at a concentration of $2\times10^5$ cells per cm$^2$ onto a 70–80% confluent monocellular layer of POAM-P1 cells, which had shortly before been exposed to 20 Gray γ-radiation. The bone marrow was cocultivated with the BOAM-P1 cells for 90 h at 37° C. in a moisture-saturated atmosphere of 10% $CO_2$ in air.

For the duration of the cocultivation, the rhesus monkey that had donated the bone marrow was conditioned for the autologous reception of the cocultivated bone marrow by means of total body irradiation with 10 Gray X-rays, divided over two equal fractions at an interval of 24 h, performed, respectively, 2 days and 1 day prior to the transplantation. On the day of the transplantation, the cocultivated bone marrow was harvested from the culture, including the bone marrow cells that had adhered to the POAM-P1 cells or to the plastic of the culture bottle during cultivation. The cells mentioned last were obtained by means of a trypsinisation. A monocellular cell suspension was prepared in a physiological salt solution with 10 μg/ml DNase I and infused into a peripheral vein.

In order to determine the in vivo regeneration capacity of the cocultivated bone marrow, use was made of the semi-quantitative assay described by Gerritsen et al. (41). This method is based on the observation that the rate at which circulating red and white blood cells regenerate after transplantation of autologous bone marrow cells in lethally irradiated rhesus monkeys depends on the size of the transplant. In particular the kinetics of the appearance of the precursors of red blood cells (reticulocytes) is a good standard in this connection. By determining haematological values in the blood system of the monkeys at regular intervals after the transplantation, it could be established (using the relation described by Gerritsen) that the modified bone marrow had preserved sufficient regenerative capacity and the cocultivation therefore had no toxic side effect.

Analysis at DNA level made it clear that long periods (up to more than a year) after the transplantation, the introduced provirus could be traced in various blood cell types (mononuclear cells and granulocytes). Especially the presence of the introduced gene in the granulocytes is considered of great importance. Since granulocytes, after being generated in the bone marrow, remain in the blood stream only a few hours before being broken down, the presence of the human ADA in these cells demonstrates that a year after transplantation the bone marrow still contains very primitive cells that give rise to the formation of ride blood cells. Also, functional expression of the introduced human ADA gene in ripe blood cells could be demonstrated. These results constitute clear proof of the fact that through the invention described here stable genetic modification of the haemopoietic system of primates can be obtained.

c) Preclinical Test of a Bone Marrow Gene Therapy Procedure in Rhesus Monkeys Which Utilizes Purified Haemopoetic Stem Cells c1) Enrichment of Primate Bone Marrow CD34+CD11b-stem Cells

Rhesus monkey bone marrow having a density lower than 1.064 g/ml was obtained as described under b). This cell population was successively depleted for cells carrying the monocytes/granulocytes-marker CD11b and enriched for cells carrying the stem cell/precursor cell-marker CD34. This was performed using immunomagnetic beads, which has been made as follows: first of all tosyl-activated polystyrene magnetic beads (Dynabeads M-450; Dynal, Oslo) were incubated for 24 h in a 0.5M borate solution pH 9.5 with 1.25 μg protein A (Pharmacia, Uppsala) per $10^6$ beads. After frequent washing in PBS containing 0.1% BSA, to the beads, now protein A-coupled, saturating concentrations of monoclonal antibodies (anti-CD11b: Mo1, Coulter Clone, Hialeah, Fl.; anti-CD34: ICH3, 43) were bound by incubating for 30 min at room temperature. Finally, the beads were frequently washed in HBSS/Hepes and stored at 4° C. until use. The bone marrow cells were incubated for 20 min at 4° C. with 7 anti-CD11b beads per cell in a concentration of $5\times10^7$ cells/ml at a maximum. Unbound CD11b-negative cells were stripped from beads and CD11b-positive cells bound thereto, using a magnetic particle collector (MPC; Dynal) and washed in HBSS/Hepes. The thus obtained cells were incubated for 20 min at 4° C. with 5 anti-CD34 beads per cell again in a concentration of $5\times10^7$ cells/ml at a maximum. After removal of the CD34-negative cells using the MPC, the bound CD34-positive cells were recovered by means of a competitive elution with an excess of immunoglobulins. To that end, the beads with CD34-positive cells were incubated for 1 h at 37° C. in HBSS/Hepes with 25% bovine plasma (Gibco, Paisley) and 500 U/ml heparin.

c2) Introduction of the Construct pLgAL(ΔMo+PyF101) Described Under a) Into Rhesus Monkey CD34+CD11b-stem Cells The introduction of the human ADA gene into rhesus monkey CD34$^+$CD11b$^-$ stem cells and the autologous transplantation procedure were performed as described under b), the only difference being that the cocultivation was performed with the previously described cell line POC-1 (12). As noted, this cell line is unstable and not very suitable for large-scale use. For this present experiment, use could still be made of an early passage which does not have a reduced titre. After transplantation all blood cell types regenerated completely, which demonstrates that the gene transfer procedure can also be performed on CD34$^+$CD11$^-$stem cells without toxic side effects. The presence of the provirus in mononuclear blood cells and in granulocytes could also be demonstrated in these monkeys during the entire experimental period (at this point 266 days and 280 days after transplantation in two monkeys) which is still in progress. Expression of the functional human ADA enzyme could also be demonstrated in blood cells of these monkeys. The enrichment for haemopoietic stem cells prior to the gene transfer did not have any demonstrable effect on the efficiency of the gene transfer to stem cells. This experiment therefore demonstrates that the results as described under b) can also be achieved when the bone marrow has been stripped from most riper cell types, which is preferred in some uses of genetic modification of bone marrow cells.

REFERENTIES

1. Anderson, W. F., 1984, Prospects for human gene therapy, Science 226: 401.
2. Belmont, J. W. and C. T. Caskey, 1986, Developments leading to human gene therapy, In Gene transfer, R. Kucherlapati, eds. Plenum press, New York and London, 411.
3. Williamson, B., 1982, Gene therapy, Nature 298: 416.
4. Williams, D. A., 1990, Expression of introduced genetic sequences in hematopoietic cells following retroviral-mediated gene transfer, Hum. Gene Ther. 1: 229.
5. Temin, H. M., 1986, Retrovirus vectors for gene transfer: efficient integration into and expression of exogenous DNA in vertebrate cell genomes, In Gene Transfer, R. Kucherlapati, eds. Plenum Press, New York, 149.
6. Temin, H. M., 1990, Safety considerations in somatic gene therapy of human disease with retrovirus vectors, Hum. Gene Ther. 1: 111.
7. Weiss, R., N. Teich, H. Varmus and J. Coffin, 1984, RNA tumor viruses, New York.
8. Miller, A. D., 1990, Retrovirus packaging cells, Hum. Gene Ther. 1: 5.
9. Danos, O. and R. C. Mulligan, 1988, Safe and efficient generation of recombinant retroviruses with amphotropic and ecotropic host ranges, Proc. Natl. Acad. Sci. U.S.A. 85: 6460.
10. Markowitz, D., S. Goff and A. Bank, 1988, A safe packaging line for gene transfer: separating viral genes on two different plasmids, J. Virol. 62: 1120.
11. Markowitz, D., S. Goff and A. Bank, 1988, Construction and use of a safe and efficient amphotropic packaging cell line, Virology 167: 400.
12. Van Beusechem, V. W., A. Kukler, M. P. W. Einerhand, T. A. Bakx, A. J. Van der Eb, D. W. Van Bekkum and D. Valerio, 1990, Expression of human adenosine deaminase in mice transplanted with hemopoietic stem cells infected with amphotropic retroviruses, J. Exp. Med. 172: 729.
13. Valerio, D., M. P. W. Einerhand, P. M. Wamsley, T. A. Bakx, C. L. Li and I. M. Verma, 1989, Retrovirus-mediated gene transfer into embryonal carcinoma cells and hemopoietic stem cells: Expression from a hybrid long terminal repeat, Gene 84: 419.
14. Anderson, W. F., P. Kantoff, M. Eglitis, J. McLachlin, E. Karson, J. Zwiebel, A. Nienhuis, S. Karlsson, R. M. Blaese, D. Kohn, E. Gilboa, D. Armentano, E. D. Zanjani, A. Flake, M. R. Harrison, A. Gillio, C. Bordignon and R. O'Reilly, 1986, Gene transfer and expression in nonhuman primates using retroviral vectors, In Cold Spring Harbor Symposia on Quantitative Biology, Volume LI, eds. Cold Spring Harbor Laboratory, New York, 1073.
15. Kantoff, P. W., A. P. Gillio, J. R. McLachlin, C. Bordignon, M. A. Eglitis, N. A. Kernan, R. C. Moen, D. B. Kohn, S. Yu, E. Karson, S. Karlsson, J. A. Zwiebel, E. Gilboa, R. M. Blaese, A. Nienhuis, R. J. O'Reilly and W. F. Anderson, 1987, Expression of human adenosine deaminase in nonhuman primates after retrovirus-mediated gene transfer, J. Exp. Med. 166: 219.
16. Bodine, D. M., K. T. McDonagh, S. J. Brandt, P. A. Ney, B. Agricola, E. Byrne and A. W. Nienhuis, 1990, Development of a high-titer retrovirus producer cell line capable of gene transfer into rhesus monkey hematopoietic stem cells, Proc. Natl. Acad. Sci. U.S.A. 87: 3738.
17. Bolivar, F., R. L. Rodrigues, P. J. Greene, M. C. Betlach, H. L. Heynecker, H. W. Boyer, J. H. Crosa and S. Falkow, 1977, Construction and characterization of of new cloning vehicles, II, A multipurpose cloning system, Gene 2: 95.
18. Vieira, J. and J. Messing, 1982, The pUC plasmids, an M13mp7-derived system for insertion mutagenesis and sequencing with synthetic universal primers, Gene 19: 259.
19. Linney, E., B. Davis, J. Overhauser, E. Chao and H. Fan, 1984, Non-function of a Moloney Murine Leukaemia Virus regulatory sequence in F9 embryonal carcinoma cells, Nature 308: 470.
20. Armentano, D., S. F. Yu, P. W. Kantoff, T. Von Ruden, W. F. Anderson and E. Gilboa, 1987, Effect of internal viral sequences on the utility of retroviral vectors, J. Virol. 61: 1647.
21. Sullenger, B. A., H. F. Gallardo, G. E. Ungers and E. Gilboa, 1990, Overexpression of TAR sequences renders cells resistant to human immunodeficiency virus replication, Cell 63: 601.
22. Borelli, E., R. Heyman, M. Hsi and R. M. Evans, 1988, Targeting of an inducible toxic phenotype in animal cells, Proc. Natl. Acad. Sci. U.S.A. 85: 7572.
23. Miller, A. D. and C. Buttimore, 1986, Redesign of retrovirus packaging cell lines to avoid recombination leading to helper virus production, Mol. Cell. Biol. 6: 2895.
24. Pellicer, A., D. Robins, B. Wold, R. Sweet, J. Jackson, I. Lowy, J. M. Roberts, G. K. Sim, S. Silverstein and R. Axel, 1980, Altering genotype and phenotype by DNA-mediated gene transfer, Science 209: 1414.
25. Southern, P. J. and P. Berg, 1982, Transformation of mammalian cells to antibiotic resistance with a bacterial gene under control of the SV40 early region promoter, J. Mol. Appl. Genet. 1: 327.
26. Blochlinger, K. and H. Diggelman, 1984, Hygromycin B phosphatransferase as a selectable marker for DNA transfer experiments with higher eucaryotic cells, Mol. Cell. Biol. 4: 2929.
27. Mulligan, R. C. and P. Berg, 1980, Expression of a bacterial gene in mammalian cells, Science 209: 1422.
28. Hartman, S. C. and R. C. Mulligan, 1988, Two dominant acting selectable markers for gene transfer studies in mammalian cells, Proc. Natl. Acad. Sci. U.S.A. 85: 8047.
29. Colbère-Garapin, F., S. Chousterman, F. Horodniceanu, P. Kourilsky and A. Garapin, 1979, Cloning of the active thymidine kinase gene of herpes simplex virus type I in *Escherichia coli* K-12, Proc. Natl. Acad. Sci. U.S.A. 76: 3755.
30. Simonsen, C. C. and A. D. Levinson, 1983, Isolation and expression of an altered mouse dihydrofolate reductase cDNA, Proc. Natl. Acad. Sci. U.S.A. 80: 2495.
31. Graham, F. L. and A. J. Van der Eb, 1973, A new technique for the assay of infectivity of human adenovirus 5 DNA, Virology 52: 456.
32. Chu, G., H. Hayakawa and P. Berg, 1987, Electroporation for the Efficient transfection of mammalian cells with DNA, Nucl. Acids Res. 15: 1311.
33. Potter, H., L. Weir and P. Leder, 1984, Enhancer-dependent expression of human k immunoglobulin genes introduced into mouse pre-B lymphocytes by electroporation, Proc. Natl. Acad. Sci. U.S.A. 81: 7161.
34. Felgner, P. L. and G. M. Ringold, 1989, Cationic liposome-mediated transfection, Nature 337: 387.
35. Felgner, P. L., T. R. Gadek, M. Holm, R. Roman, H. W. Chan, M. Wenz, J. P. Northrop, G. M. Ringold and M. Danielsen, 1987, Lipofection: A highly efficient, lipid-mediated DNA-transfection procedure, Proc. Natl. Acad. Sci. U.S.A. 84: 7413.
36. Bestwick, R. K., S. L. Kozak and D. Kabat, 1988, Overcoming interference to retroviral superinfection results in amplified expression and transmission of cloned genes, Proc. Natl. Acad. Sci. U.S.A. 85: 5404.

37. Kozak, S. L. and D. Kabat, 1990, Ping-pong amplification of a retroviral vector achieves high-level gene expression: human growth hormone production, J. Virol. 64: 3500.

38. Chen, C. and H. Okayama, 1987, High-efficiency transformation of mammalian cells by plasmid DNA, Mol. Cell. Biol. 7: 2745.

39. Dicke, K. A., G. Tridente and D. W. Van Bekkum, 1969, The selective elimination of immunologically competent cells from bone marrow and lymphocyte cell mixtures, III, In vitro test for the detection of immunocompetent cells in fractionated mouse spleen cell suspensions and primate bone marrow suspensions, Transplantation 8: 422.

40. Burger, H., R. W. Van Leen, L. C. J. Dorssers, N. L. M. Persoon, P. J. Lemson and G. Wagemaker, 1990, Species specificity of human interleukin-3 demonstrated by cloning and expression of the homologous rhesus monkey (Macaca mulatta) gene, Blood 76: 2229.

41. Gerritsen, W. R., G. Wagemaker, M. Jonker, M. J. H. Kenter, J. J. Wielenga, G. Hale, H. Waldmann and D. W. Van Bekkum, 1988, The repopulation capacity of bone marrow grafts following pretreatment with monoclonal antibodies against T lymphocytes in rhesus monkeys, Transplantation 45: 301.

42. Mansour, S. L., K. R. Thomas and M. R. Capecchi, 1988, Disruption of the proto-oncogene int-2 in mouse embryo-derived stem cells: a general strategy for targeting mutations to non-selectable genes, Nature 336: 348.

43. Watt, S. M., K. Gatter, A. J. W. Furley, F. E. Katz, L. E. Healy, L. J. Atass, N. J. Bradley, D. R. Sutherland, R. J. Levinsky and M. F. Greaves, 1987, Distribution and epitope analysis of the cell membrane glycoprotein (HPCA-1) associated with human hemopoietic progenitor cells, Leukemia 1: 417.

We claim:

1. A method for preparing primate bone marrow cells containing a DNA sequence of interest, the method comprising, a) isolating bone marrow cells from a primate, b) co-culturing the bone marrow cells with retrovirus producer cells which produce an amphotropic retroviral vector, wherein the retroviral vector contains the DNA sequence of interest, and c) harvesting from the co-culture both non-adherent and adherent cells which contain the DNA sequence of interest.

2. The method according to claim 1, wherein the retroviral vector is an MuLV retroviral vector.

3. The method according to claim 2, wherein the retroviral vector comprises two LTRs from MuLV and the 5' region of the gag gene of MuLV.

4. The method according to claim 3, wherein the MuLV is Mo-MuLV and at least the 3' LTR is a hybrid LTR, where the PyF101 enhancer replaces the Mo-MuLV enhancer.

5. The method according to claim 4, wherein the retroviral vector is pLgXL (Mo+PyF101), where X represents the DNA sequence of interest.

6. The method according to claim 1, wherein the producer cells are mammalian cells that contain at least one packaging construct that expresses the gag, pol and env gene of MuLV.

7. The method according to claim 6, wherein the env gene is from an amphotrophic MuLV.

8. The method according to claim 6, wherein the producer cells contain two different packaging constructs that together express the gag, pol and env genes of MuLV, where the constructs are contained in at least two different eukaryotic expression vectors.

9. The method according to claim 6, wherein the producer cells additionally contain a selectable marker.

10. The method according to claim 6, wherein the producer cells are GP+envAM12.

11. The method according to claim 1, wherein the producer cells contain more than one copy of the retroviral vector integrated into the genome of each the producer cells.

12. The method according to claim 1, wherein the co-cultivation is in the presence of serum and at least one hematopoietic growth factor.

13. The method according to claim 1, wherein the bone marrow cells are enriched for hematopoietic stem cells by removal of non-stem cells prior to co-cultivation.

* * * * *